US00PP12696P2

(12) United States Plant Patent
Karniel

(10) Patent No.: US PP12,696 P2
(45) Date of Patent: Jun. 11, 2002

(54) TABLE SEEDLESS GRAPE PLANT NAMED 'EARLY SUGAR'

(76) Inventor: Shachar Karniel, 48 Nili Boulevard, Zichron Yackov 30900 (IL)

( * ) Notice: Subject to any disclaimer, the term of this patent is extended or adjusted under 35 U.S.C. 154(b) by 0 days.

(21) Appl. No.: 09/534,826

(22) Filed: Mar. 23, 2000

(51) Int. Cl.[7] ..... A01H 5/00

(52) U.S. Cl. ..... Plt./207

(58) Field of Search ..... Plt./207, 205

*Primary Examiner*—Bruce R. Campell
*Assistant Examiner*—June Hwu
(74) *Attorney, Agent, or Firm*—Christie, Parker & Hale, LLP

(57) ABSTRACT

Described is a new grape variety that produces substantially uniform, large white table grapes on a productive plant.

1 Drawing Sheet

BACKGROUND OF THE INVENTION

The invention relates to a new and distinct variety of the *Vitis vinifera L.* species which produces white seedless table grapes.

The new variety is the result of a cross of the variety 'Yantar' (unpatented) as seed parent, and the variety 'Novomuscat Seedless' (unpatented) as pollen parent followed by embryo rescue and budwood propagation by cuttings. The variety has been asexually reproduced by budwood propagation in Zichron Yackov, Israel.

COMPARISON WITH PARENTS

The new variety distinguishes from its parent variety 'Yantar' in color and is a seedless selection, ripening very early, with an ovate shape of berry and a slight Muscat taste, whereas 'Yantar' is a white creamy color variety, early seeded and ripens later than the new variety.

The new variety distinguishes from its parent variety 'Novomuscat' in berry size and shape and taste, whereas 'Novomuscat' has small uneven berries and a very strong Muscat taste.

BRIEF DESCRIPTION OF ILLUSTRATIONS

The accompanying illustration shows typical specimens of the vegetative growth and berries of the new variety depicted in color as nearly true as it is reasonably possible to make the same in a color illustration of this character.

DESCRIPTION OF THE NEW VARIETY

The following is a detailed description of 11 year-old plants of the new variety grown outdoors in Zichron Yackov, Israel, in April to September on their own rootstock. The color terminology used is in accordance with The Royal Horticultural Society Colour Chart. Physiological and morphological characteristics described with reference to the standard guidelines of I.P.G.R.I., U.P.O.V., O.I.V. (1997). Descriptors for GRAPEVINE (Vitis spp.), International Union for the Protection of New Varieties of Plants, Geneva, Switzerland/Office International de la Vigne et du Vin, Paris, France/International Plant Genetic Resources Institute, Rome, Italy, guidelines. Phenotypic expression may vary depending on environmental, climate and cultural conditions. The referenced varieties 'Perlette Seedless', 'Queen of Vineyards', 'Flame Seedless' and 'Thompson Seedless' are not known to be patented.

Vine:

*Size.*—Medium spread canopy with medium leaf size.
*Form.*—Erect (UPOV 6.1.5/1).
*Vigor.*—Moderate vigor influenced by the crop.
*Time of sprouting.*—Very early before 'Perlette Seedless'.
*Young vine — productivity.*—Heavy production, average about 40–50 bunches per vine in commercial production; without thinning about 70–80 bunches per vine, 2–3 bunches per shoot.

Trunk: 11 year-old vine in Israeli farming conditions.

*Size.*—Small to medium similar to 'Queen of Vineyards' ranges from 38.6 mm (1.52 inches) to 55 mm (2.2 inches).
*Trunk.*—(About 4 to 6 inches).
*Surface texture.*—Rough with a fibrous, shaggy exterior upper side color Brown Group color near 200C, bottom side color from Grayed-Orange Group near 166B.

Canes:

*Size.*—Mature cane about 0.6–1.0 cm width (about ⅜ inch).
*Number.*—Eleven-year, quadrilateral cordon about 25–30 spurs, 60–70 shoots per vine.
*Diameter.*—About 0.6–1.0 cm.
*Color.*—Mature third year, cane surface is relatively smooth with yellowish brown color cane; Greyed-Orange Group near 175C. This color checked on internode 3 to 4 from the cane base; Red-Burgundy color (near 187C) of strips along the cane.
*Form.*—Straight, upright; nodes upright, pointed.
*Nodes.*—Size: Width at center about 1.2 cm (9/16 inch). Internode size: Width at center about 0.6–0.8 cm (7/16 inch). Internode length: Length about 5–10 cm.
*Number of tendrils.*—Tendrils in almost every node; horizontal to upright.
*Tendril thickness.*—About 0.1–0.3 cm.
*Tendril length.*—Medium, about 19–21 cm (4 inches).
*Tendril texture.*—Woody.

Flowers: Male and female; fully developed (UPOV 6.2.1/3), self fertile; perfect.

*Date of bloom.*—About 12–15 days before 'Perlette Seedless'; about 3 weeks before 'Flame Seedless', when under similar conditions.

*Filament.*—Length about 5/32 inch; color Yellow-Green Group near 145D.

*Anther.*—Color Yellow Group near 5C; size 1/32 inch.

*Pistil.*—Color Yellow-Green Group near 145B; length about 3/32 inch.

*Flower stem.*—Length about 7/32 inch; color Yellow-Green Group near 145C.

*Flower type.*—Male and female fully developed (U.P.O.V. 6.2.1/3).

*Stamens.*—Are taller than pistils (ovaries) which make the flower self-fertile. Date first bloom: In average cold spring region — 28 April. Date last bloom: In average cold spring region — 15 May. Average flower size: Normal. Pistil size: Average length of pistil and pedicel (ovary+pedicel) is about 3/32 inch. Color of Pistil: (Ovary) Light Yellow-Green, Yellow Green Group near 145B. Color of Stamen: Yellow-Cream (Yellow Group near 5C). Stamen length: Average length is about 6/32 inch. Stamen number: About 5 stamen in one flower bud. Pedicel: Short, less than 1/16 inch with creamy color, Yellow Group near 10D.

Leaves:

*Size.*—The mature leaf is large size, the young leaf is small size (recorded on the first 4 distral unformed leaves — U.P.O.V. — 6.1.16).

*Average length.*—Mature leaf: About 5 5/16 inches. Young Leaf: About 2 5/16 inches.

*Average width.*—Mature leaf: About 7 4/16 inches. Young Leaf: About 3 1/16 inches.

*Thickness.*—Normal.

*Form.*—Pentagonal (U.P.O.V. — 6.1.22/3).

*Color dorsal surface.*—Mature leaf: Green Group near 137A. Young Leaf: Green Group near 144A.

*Color ventral surface.*—Mature leaf: Green Group near 137C. Young Leaf: Green Group near 144B.

*Color.*—Near 184A anthocyanin coloration. Often well developed small cluster of flower buds on tip.

*Texture dorsal surface.*—Mature leaf: Smooth surface without hairs and very weak, anthocyanin coloration of main veins (U.P.O.V. — 6.1.24/1). Young Leaf: Smooth and shiny surface without hairs and very weak coloration of main veins (U.P.O.V. — 6.1.24/1).

*Texture ventral surface.*—Mature leaf: Fairly smooth with very sparse prostate hairs in main veins (U.P.O.V. — 6.1.37/1). Young Leaf: Shiny smooth with space prostrate hairs on main veins (UPOV — 6.1.20/1).

*Number of lobes.*—About five (UPOV — 6/1/23/3).

*Terminal lobe — form.*—Oval larger lobe compare to the leaf general size with deep basal sinuses in both sides.

*Petiolar color.*—Yellow-Green (Yellow-Green Group near 144C) with anthocyanin coloration — Red striped (Grayed-Purple Group near 185C).

*Petiolar sinus depth.*—Average about 7/8 inch to 1 inch with the present tooth at petiole sinus (U.P.O.V. — 6/1/31/1).

*Petiole length.*—About 4 5/8 inch.

*Petiolar sinus shape.*—Slightly open (U.P.O.V. 6.1.30/4).

*Basal sinus.*—Deep, lobes slightly overlapped (U.P.O.V. — 6/1/33/3).

*Lateral sinus.*—Medium deep, lobes slightly overlapping (U.P.O.V. — 6.1.33/3).

*Margin form.*—Undulate (U.P.O.V. — 6.1.25/5).

*Teeth.*—Mixture of both sides straight and both sides convex (U.P.O.V. — 6.1.27/5), medium length and medium ratio between length/width of teeth (U.P.O.V. — 6.1.29/5).

*Shoot tip.*—Form of Tip: Fully open (U.P.O.V. — 6.1.1/5) with the weak anthocyanin coloration of the tip (Grayed-Red Group near 182C) (U.P.O.V. — 6.1.2/3) and dense prostrate.

*Shoot.*—Upright with fully open tip, with up to 2 consecutive tendrils, round with intensive anthocyanin coloration on dorsal side (Grayed-Red Group near 187A) and Yellow-Green (Yellow-Green Group near 144A) with Red strips on the ventral side.

*Leaf blade.*—Serrated margin with average length about 7/8 inch to 1 4/8 inches and average width about 7/8 inch to 1 3/8 inches.

*Dorsal surface.*—Reddish (U.P.O.V. — 6.1.16/7) Yellow-Green (Yellow-Green Group near 145A) with intensive anthocyanin coloration (Grayed-Purple Group near 184C) Very sparse prostrate hairs between the veins (U.P.O.V. — 6.1.17/1) and sparse prostrate hairs on main veins (U.P.O.V. — 6.1.19/3), about 5 lobes with very deep lateral sinuses.

*Ventral surface.*—Reddish (U.P.O.V. — 6.1.16/7) with sparse prostrate hairs on main veins.

Tendrils:

*Number.*—Up to 2 consecutive tendrils on the shoot (U.P.O.V. 6.1.14).

*Thickness.*—Young: About 1/16 inch.

*Length.*—Average short about 4 7/8 inches; the base part without "V" — Medium size (U.P.O.V. 6.1.15/5). Mature: About 9 1/16 inches. Young: About 6 1/16 inches.

*Form.*—Open "V" shape with 1 or 2 curling in the end of the tendril and often with well developed small cluster of flower buds in the end of the tendril.

*Texture.*—Slightly firm but no woody; Young tendril color — Yellow-Green (Yellow-Green Group near 144C) often with anthocyanin coloration (Green-Purple Group near 184A); Developed tendril color, Yellow-Green Group near 144C and Grayed-Purple Group near 185B lines.

Fruit:

*Maturity at time of description.*—At maturity fruit advantageously treated with gibberellic acid are oval, large berries, yellowish green with slight Muscat flavor; the berries are equal in size with very little shatter; the berries are well attached to the cup stem; average weight of berry treated with Gibberellic acid about 8.0–8.5 gr.; average weight of berry not treated with Gibberellic acid about 3–4 gr.

*Size.*—Untreated about 2.5 cm; treated about 4–6 cm (13/15 to 15/16 inch).

*Sugar/acid ratio.*—Treated with Gibberellic acid about 16 to 18 brix; not treated about 16 to 19 brix.

*Ripening date.*—Very early; about 5 days before 'Perlette Seedless'.

*Skin thickness.*—Slightly more thicker than 'Thompson seedless' but definitely lighter than 'Superior Seedless'.

*Color of skin.*—Yellowish-Green to creamy bright near 151A.

*Color of pulp.*—Clear white, pulp ring around the skin about 1/8 inch; color Green-Yellow Group near 1C; entire pulp true the center color Green-Yellow Group near 1B.

*Texture of berry pulp.*—Meaty and juicy, slight Muscat flavor.

*Presence of seeds.*—Seed trace at maturity light green; size up to about 4 mm, 1/8 inch, when fruit is held on the vine or kept in cold storage seed traces may turn light brown.

*Storage quality.*—Stores well up to about 3 to 4 weeks without changes in eating qualities and shape, keeps well.

*Shipping quality.*—No shatter, no discoloration, no shriveling.

Cluster:

*General description.*—Bunch has conical shape as grown.

*Size.*—Length is about 25–30 cm (10 to 12 inches); width about 15–20 cm (6 to 8 inches; about 450–800 gr per bunch.

*Berry diameter.*—Average about 21 to 24 mm (13/16 to 15/16 inch).

*Berry skin thickness.*—Medium.

*Berry skin texture.*—Smooth; meaty and crunchy.

*Flesh texture.*—Meaty.

*Juice production.*—Juicy.

*Flavor.*—Light Muscat on full ripening.

*Berry size uniformity.*—Generally very uniform in the bunch in the range of 13/16 to 15/16 inch and from bunch to bunch.

*Peduncle length.*—Medium to long; about 38 mm (1½ inches).

*Peduncle thickness.*—Medium thickness; about 5 mm (31/16 inch).

*Pedicel length.*—Medium; ribbed bunch-top shoulders about 12 mm (¼ inch); bottom part of bunch is about 8 mm (5/16 inch).

*Pedicel diameter.*—Thick for ribbed about 1.2 mm (1/32 inch).

*Brush length.*—About 6 mm (3/16 inch).

*Brush color.*—Yellowish, color Green Group near 150B.

*Seeds.*—At maturity light green.

Use: For table grapes growing and marketing.

Uniqueness: Ripening time very early compared to 'Perlette Seedless' and 'Flame Seedless'.

*Productivity.*—Average about 40–50 bunches per vine, stable productivity, very fertile.

*Resistance to fruit rotting.*—Fairly good.

*Storage capacity.*—Very good with no decadence.

*Bunches.*—Berry uniform in size under most climatic conditions especially when grown under climatic conditions such as in hot areas which trigger the development of non-uniform berries within cluster and between clusters in other varieties.

Disease resistance: Same as most of common varieties in Israel of the *Vitis vinifera;* namely some sensitivity to mildew.

I claim:

1. A new and distinct white seedless grape plant known as 'Early Sugar' substantially as shown and described.

* * * * *

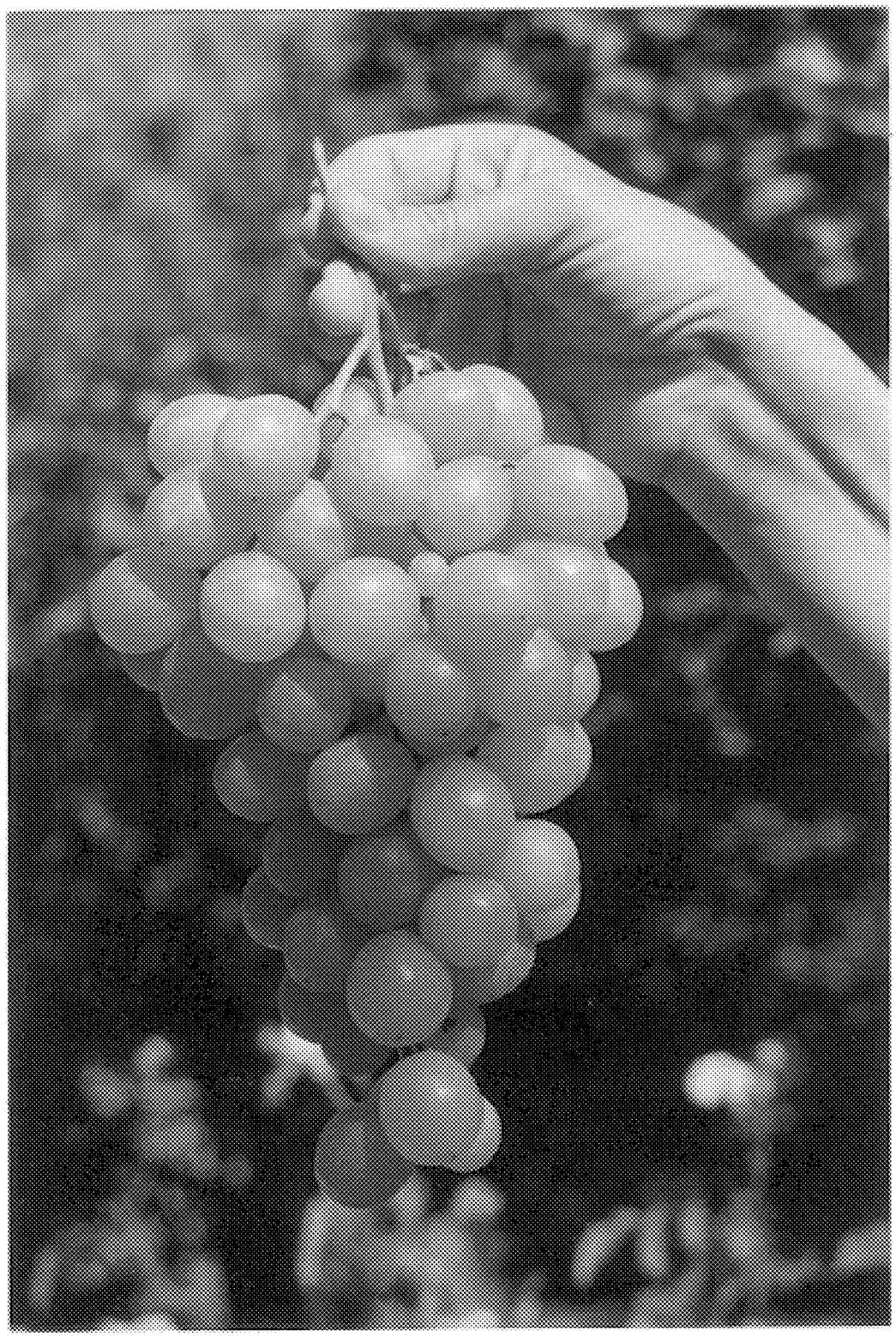

UNITED STATES PATENT AND TRADEMARK OFFICE

CERTIFICATE OF CORRECTION

PATENT NO. : PP 12,696 P2
DATED : June 11, 2002
INVENTOR(S) : Shachar Karniel

It is certified that error appears in the above-identified patent and that said Letters Patent is hereby corrected as shown below:

Title page,
Item [54], Title, should read -- TABLE SEEDLESS GRAPE PLANT NAMED 'GRAPAES' --.

Column 1,
Line 1, under "Summary of the Invention," replace "'Early Sugar'" with
-- GRAPAES --.
Line 12, insert SUMMARY OF THE INVENTION as follows:
-- SUMMARY OF THE INVENTION The new variety 'Early Sugar' is a large, white seedless table grape with large production, e.g., about 40 to 50 bunches per vine, and an average of about two to three bunches per shoot.

Asexual reproduction by micropropagation of the new variety as performed in Zichron Yackov, Israel, shows that the foregoing and other distinguishing characteristics come true to form and are established and transmitted through succeeding propagations. --.

Column 2,
Line 9, replace "*Young vine — productivity*." with
-- *Young vine — cane — productivity*. --.

Column 3,
Line 14, under Leaves, after "*Color*. —" delete "Near 184A" and insert -- Yellow-Green Group near 144C with Green-Purple Group near 184A --.
Line 23, under Leaves, replace "prostate" with -- prostrate --.

Column 4,
Line 1, under Tendrils, replace "(U.P.O.V. 6.1.14)" with -- (U.P.O.V. — 6.1.14) --.
Line 4, under Tendrils, replace "(U.P.O.V. 6.1.15/5)" with -- (U.P.O.V. — 6.1.15/5) --.
Line 10, under Tendrils, replace "no woody" with -- not woody --.

UNITED STATES PATENT AND TRADEMARK OFFICE

CERTIFICATE OF CORRECTION

PATENT NO. : PP 12,696 P2
DATED : June 11, 2002
INVENTOR(S) : Shachar Karniel

It is certified that error appears in the above-identified patent and that said Letters Patent is hereby corrected as shown below:

Column 6,
Last line, replace "'Early Sugar'" with -- GRAPAES --.

Signed and Sealed this

Nineteenth Day of November, 2002

*Attest:*

*Attesting Officer*

JAMES E. ROGAN
*Director of the United States Patent and Trademark Office*